(12) United States Patent
Wilson et al.

(10) Patent No.: US 8,343,474 B2
(45) Date of Patent: Jan. 1, 2013

(54) SUBSTITUTED ORGANOPOLYSILOXANES AND USES THEREOF

(75) Inventors: John Robert Howe Wilson, London (GB); Alice Caroline Sullivan, London (GB); Siud Pui Man, London (GB)

(73) Assignee: Phosphonics Ltd., Oxford (GB)

( * ) Notice: Subject to any disclaimer, the term of this patent is extended or adjusted under 35 U.S.C. 154(b) by 920 days.

(21) Appl. No.: 12/278,939

(22) PCT Filed: Feb. 9, 2007

(86) PCT No.: PCT/EP2007/001137
§ 371 (c)(1),
(2), (4) Date: Mar. 26, 2009

(87) PCT Pub. No.: WO2007/090676
PCT Pub. Date: Aug. 16, 2007

(65) Prior Publication Data
US 2009/0220449 A1    Sep. 3, 2009

(30) Foreign Application Priority Data
Feb. 10, 2006 (EP) ........................................ 0602811

(51) Int. Cl.
*A61K 31/765* (2006.01)
*C08G 77/00* (2006.01)
*C08J 5/00* (2006.01)
*C12N 11/08* (2006.01)

(52) U.S. Cl. ............ 424/78.37; 528/26; 528/30; 528/31; 521/25; 210/660; 210/681; 210/688; 530/402; 435/180

(58) Field of Classification Search ............... 528/26, 528/30, 31; 521/25; 210/660, 681, 688; 530/402; 435/180; 424/78.37
See application file for complete search history.

(56) References Cited

U.S. PATENT DOCUMENTS
2003/0199619 A1   10/2003   Cruse

FOREIGN PATENT DOCUMENTS
WO    WO 2006 013060    2/2006

OTHER PUBLICATIONS
International Preliminary Report on Patentability for PCT/EP2007/001137.

*Primary Examiner* — Porfirio Nazario Gonzalez
(74) *Attorney, Agent, or Firm* — Lathrop & Gage LLP; Brian C. Trinque; Giulio A. DeConti

(57) ABSTRACT

The invention relates to new compounds of Formula 1: $[(O_{3/2})Si\,CH_2CH_2SX]_a\,[Si(O_{4/2})]_b[Si(O_{3/2}v)]_c$. The compounds are useful as scavengers for the removal of unwanted organic and inorganic compounds, for solid phase extraction, for solid phase synthesis, for acid and metal mediated heterogeneous catalysis, for metal ion abstraction and for the immobilization of bio-molecules.

44 Claims, No Drawings

SUBSTITUTED ORGANOPOLYSILOXANES AND USES THEREOF

The invention relates to new organopolysiloxanes and their use for example as cation and anion exchangers, organic and inorganic compound scavengers, solid phase purification or extraction materials, immobilisation materials for bio-molecules, anti-microbial agents, hydrophilicity modifiers, flameproofing agents, antistatic agents, coatings for biomedical devices, water repellent films and coatings, solid phase synthesis materials and chromatography materials. The invention also relates to precursors of these new products and processes for their production.

The use of functionalised solids is growing rapidly for many different applications such as solution phase synthesis, solid phase synthesis, solid phase extraction, catalysis, catalyst supports, product purification and the immobilisation of bio-molecules. In these applications the advantages of functionalised solids are ease of manipulation, simple separation from the rest of the medium by filtration and regeneration and reuse. Key requirements for these functionalised solids are excellent physical and chemical stability over a wide range of operating conditions, broad solvent applicability, fast kinetics—fast and easy access to the functional groups and functional groups with high intrinsic activity for the desired application. In addition the preparation of these functionalised materials has to be simple from readily available reagents. Finally it is highly advantageous if the functional groups can be readily transformed into different functionalised materials that can be used for other applications.

As a consequence of stricter environmental regulations there is a growing requirement for more effective systems for the removal and recovery of toxic and hazardous chemicals from many sources including a wide spectrum of contaminated products, active pharmaceutical ingredients (API), solvents, potable water and aqueous based wastes and from contaminated waters. For example in the pharmaceutical industry metal catalysts are increasing being used in the manufacture of APIs or their intermediates. Given the toxicity of these metals very low residual levels have to be achieved in the API. In the preparation of compound libraries for biological evaluation simple and quick processes are required to purify reaction mixtures in order to screen thousands of compounds to identify leads for optimisation and development programmes. The electronics industry has a particular need for ultra pure water with very low levels of both cations and anions. Other industries such as the nuclear industry and the electroplating industry generate substantial quantities of water-based effluent that are heavily contaminated with undesirable metal ions.

Substituted polystyrene derivatives are an important class of materials being used for scavenging metal ions and organic compounds. The chemical and physical properties of a variety of such polystyrene based systems are described in the Bio-Rad Life Science Research Products catalogue 1998/99, pages 56-64. However one limitation of these polystyrene resins is that a range of chemical functionality cannot be readily attached to these organic polymers due to the physical limitations of these polymers and the range of chemistry that can be used to attaché functional groups onto the aromatic rings. In addition the physical and chemical properties of these polystyrene resins may possess disadvantages, for example poor chemical stability and thermal stability, believed to be due to the organic polymeric backbone. Additional problems for example swelling and shrinking in organic solvents as well as the production of highly coloured unwanted side products may also be encountered. Generally, due to their poor thermal stability, these polystyrene resins cannot be used for any length of time above 80° C., thus limiting their general applicability.

Inorganic polymer systems such as silica, aluminium oxide and titanium oxide have also been disclosed as functionalised materials. Active functional groups or metals can be attached by a variety of means to these systems. However a number of problems may be encountered where the functional groups are only physically adsorbed for example low functional group loading along with limitations in the range of solvents that can be used and removal of the functional groups on use or on standing. This is believed to be due to the rather weak attachment between the functional group and the surface atoms on the support. Building the functional group into the framework may provide a more robust material and may also permit higher functional group loadings. However in this approach there is a significant lack of readily available starting materials as well as precursors for preparing such starting materials. In addition there are limited synthetic methodologies for the preparation of suitable starting materials from available precursors. A need exists to provide new synthetic methods as well as starting compounds in order to make such functionalised materials.

Functionalised solid materials are used in solution phase organic synthesis to aid rapid purification and workup. These materials, also known as scavengers, may remove excess reagents and side products. Typically, a scavenger is added to a solution to quench and selectively react with excess or unreacted reagents and reaction side products. The unwanted chemicals now attached to the functionalised materials are removed by simple filtration. This simple process circumvents the standard purification methodologies of liquid-liquid extraction, chromatography and crystallisation. Substituted polystyrene derivatives are known for use as scavengers but have a number of limitations such as lack of thermal stability, swelling and shrinking in organic solvents and a limited range of functional groups.

In solid phase synthesis substituted polystyrene derivatives are the main class of materials being used and likewise these materials suffer the same limitations as described above. The use of functionalised silica materials for this application is limited by the availability of suitable functionalised materials.

Due to their toxicity there is a growing requirement for more effective systems for the removal and recovery of cations and anions including a wide spectrum of contaminated products, active pharmaceutical ingredients (API), solvents, potable water and aqueous based wastes and from contaminated waters. Polymers having an organic, partly cross-linked polystyrene backbone with sulfonate groups attached to some of the phenyl rings are known for use as cation exchangers for removing metal ions from solution. However these resins have a limited spectrum of activity, poor selectivity and are not able to remove the metal ion from metal complexes. In addition the physical and chemical stability and other properties of these materials for example due to the organic nature of the polymeric backbone, may adversely affect their use in cation exchange applications.

Strong acidic cation exchangers based on sulfonic acid groups attached to an organopolysiloxane backbone have been described in U.S. Pat. No. 4,552,700 and U.S. Pat. No. 5,354,831. The reported materials have a general formula of $(O_{3/2}Si-R^1-SO_3^-)_xM^x$ where $R^1$ is an alkyl or cycloalkyl fragment, M is hydrogen or a mono to tetravalent metal ion and where the free valences of the oxygen atoms being saturated by silicon atoms of other groups of this formula and/or by cross-linking bridge members such as $SiO_{4/2}$, $R^1SiO_{3/2}$, TiO$_{4/2}$, AlO$_{3/2}$, etc. Whilst these materials can act as cation exchangers it is generally recognised that sulfonic acid groups are limited in their effectiveness to complex with a range of metals and in comparison to other functional groups. In addition the sulfonate group is also limited by the fact that it is a mono anion and thus more of these functional groups are needed to bind to di and multivalent metal ions compared to other functional groups. These materials are also expensive to prepare. In our earlier patent application PCT/GB 0200069 we reported on organopolysiloxanes containing phosphonic groups. These materials demonstrate high intrinsic activity for the removal of metal ions. A range of other functionalised materials is needed particularly to separate specific metal ions from various environments.

Anions such as arsenates, chromates, permanganates, borates and perchlorates pose many significant problems to the environment and health. For example arsenates, chromates and permanganates are highly toxic and so their concentrations in water or other medium has to be very carefully controlled. New materials with very high affinity for such anions are needed in order to achieve very low acceptable limits.

Precious metal mediated reactions enable the organic chemist to conduct a wide range of reactions used in the manufacture of products for a number of industries. Typical reactions include Suzuki, Heck, oxidations and reductions and metals and their complexes such as platinum, palladium and rhodium are extensively used. A major problem encountered with the use of these systems is the significant loss of these expensive and highly toxic metals. Furthermore in the production of active pharmaceutical agents (APIS) using such metal mediated reactions, it is found that the metal invariably complexes to the desired API and residual metal contents in the range of 600-1000 ppm are not uncommon. The current target for palladium, platinum, rhodium and nickel is less than 5 ppm. Various methods have been tried to reduce the residual palladium content, most unsuccessfully. Selective re-crystallisation leads to only a slight lowering of metal content. A lower yield of the API is a significant unwanted side effect of this process. Attempts to reposition the precious metal catalysed reaction from the final to an earlier step leads also to a slight but not significant lowering of metal content. Attempts to pass a solution of the API through a medium containing a metal exchanger such as a functionalised polystyrene resin have also been largely unsuccessful. Alternative and more costly processes have been tried—washing with an aqueous solution of a suitable metal chelator. A number of such reagents have been used with only limited success. Thus there is a need to design new functionalised materials that have very high affinity for precious metals and can readily remove them from tightly bound complexes. Furthermore given the structural diversity of APIs it is necessary to have a range of functionalised materials with different structures and high affinity in order to provide an effective solution.

The inventors have discovered a class of compounds which have a desirable combination of characteristics and make them suitable for use in a range of applications including acting as scavengers for inorganic and organic compounds, solid phase purification or extraction materials, ion exchange materials, catalysts, catalyst immobilisation supports, immobilisation materials for bio-molecules, anti-microbial agents, hydrophilicity modifiers, flameproofing agents, antistatic agents, solid phase synthesis materials and chromatography materials, or which are precursors for these.

A compound of formula 1:

$$[(O_{3/2})Si\,CH_2CH_2SX]_a\,[Si(O_{4/2})]_b\,[Si(O_{3/2}V)]_c$$

wherein X is selected from
CH$_2$A;
[CH$_2$CH$_2$NR$^1$]$_p$ R$^2$;
CHCOX$_1$CH$_2$COX$_2$
(CH$_2$)$_e$CO Y[CO(CH$_2$)$_e$SCH$_2$CH$_2$Si(O$_{3/2}$)]$_m$[CO(CH$_2$)$_e$SH]$_n$ and wherein A is the residue of an amino acid or a derivative or a salt of an amino acid of formula

CHNR$^1$R$^2$COX$_3$;

R$^1$ and R$^2$ are independently selected from hydrogen, C$_{1-22}$ alkyl group, C$_{1-22}$ alkyl group, C$_{1-22}$ acyl group and a C$_{1-22}$ alkaryl group;

X$_3$ is selected from OR, NR$^1$R$^2$, an amino acid and a protein;

R is selected from hydrogen, a metal ion, a C$_{1-22}$ alkyl group e is 1 or 2;
p is 1 to 100;
X$_1$ and X$_2$ are independently selected from OR and N R$^1$ R$^2$
Y is a polyol moiety having z hydroxyl groups wherein z or fewer hydroxyl groups are deprotonated, m and n are, independently, less than z such that m+n+1 is less than or equal to z and m+n+1 hydroxyl groups of the polyol are deprotonated;

V is a group which is optionally substituted and selected from a C$_{1-22}$-alkyl group, C$_{2-22}$-alkenyl group, a C$_{2-22}$-alkynyl group, an aryl group a C$_{1-22}$ alkylaryl sulphide group, a sulfoxide, a sulfone, an amine, a polyalkyl amine, a phosphine and other phosphorous containing group; the free valences of the silicate oxygen atoms are saturated by one or more of:
a silicon atom of other groups of Formula 1, hydrogen, a linear or branched C$_{1-22}$-alkyl group, an end group R$^3_3$M$^1$O$_{1/2}$, a cross-linking bridge member or by a chain R$^3_q$M$^1$(OR$^4$)$_g$O$_{k/2}$ or Al(OR$^4$)$_{3-h}$O$_{h/2}$ or R$^3$Al(OR$^4$)$_{2-r}$O$_{r/2}$;
wherein
M$^1$ is Si or Ti;
R$^3$ and R$^4$ are independently selected from a linear or branched C$_{1-22}$ alkyl group, an aryl group and a C$_{1-22}$ alkylaryl group;
k is an integer from 1 to 3, q is an integer from 1 to 2 and m is an integer from 0 to 2 such that g+k+q=4;
h is an integer from 1 to 3; and
r is an integer from 1 to 2;
or an oxo metal bridging systems where the metal is zirconium, boron, magnesium, iron, nickel or a lanthanide;
a, b and c are integers such that the ratio of a:b is from 0.00001 to 100000 and a and b are always greater than 0 and when c is greater than 0, the ratio of c to a+b is from 0.00001 to 100000.

Where an end group and/or cross linker and/or polymer chain is used, it is preferred that the ratio of end group, cross linker or polymer chains to a+b+c is from 0 to 999:1 preferably 0.001 to 999:1 and especially 0.01 to 99:1.

Advantages of the new scavengers for inorganic and organic compounds, solid phase extraction or purification materials, catalysts, catalyst immobilisation supports, biomolecule immobilisation supports, anti-microbial agents, hydrophilicity modifiers, flameproofing agents, antistatic agents, solid phase synthesis materials and chromatography materials, and ion exchanger materials based on compounds of Formula 1 include high intrinsic activity of particular functional groups for specific applications and that the functional group or groups can be tuned to have either a high or low level of loading according to the requirements of the user. Other advantages include high thermal stability, fixed and rigid structures, good stability to a wide range of chemical conditions, insolubility in organic solvents, high resistance to ageing, easily purified and high reusability. In addition the processes for the preparation of compounds of Formula 1 are very flexible, allowing a wide range of functionalised materials to be made from a small number of common intermediates and also the porosity of the materials can be varied from micro to macro porous and the loading of the functional groups as well as the other substituents in the fragment V to be varied as needed. Compounds of Formula 1 have the added advantage of their respective functional groups being firmly attached to a very stable and inert medium. Furthermore compounds of Formula 1 have the added advantages of a very high affinity for both cations and anions coupled with fast kinetics thus enabling very rapid removal of toxic compounds or impurities to very low levels. In addition compounds of Formula 1 can be used as heterogeneous catalysts to conduct a number of chemical transformations and posses the key advantages of being easily separated from the reaction mixture by filtration and also of being recycled and reused.

The optionally substituted linear or branched group selected from $C_{1-22}$-alkyl, $C_{2-22}$-alkenyl, $C_{2-22}$-alkynyl group, an aryl and $C_{1-22}$-alkylaryl group, $R^{1-4}$ groups may independently be linear or branched and/or may be substituted with one or more substituents but preferably contain only hydrogen and carbon atoms. If a substituent is present, it may be selected from nitro, chloro, fluoro, bromo, nitrile, hydroxyl, carboxylic acid carboxylic esters, sulfides, sulfoxides, sulfones, $C_{1-6}$-alkoxy, a $C_{1-22}$-alkyl or aryl di substituted phosphine, amino, amino $C_{1-22}$-alkyl or amino di ($C_{1-22}$-alkyl) or $C_{1-22}$-alkyl phosphinic or phosphonic group.

Preferably, the optionally substituted linear or branched group selected from $C_{1-22}$-alkyl, $C_{2-22}$-alkenyl, $C_{2-22}$-alkynyl group, an aryl and $C_{1-22}$-alkylaryl group, $R^{1-4}$ are independently selected from linear or branched $C_{1-22}$ and desirably $C_{1-12}$-alkyl, $C_{2-22}$- and desirably $C_{2-12}$-alkenyl, aryl and a $C_{1-22}$-alkylaryl group and it is especially preferred that these groups are independently selected from a linear or branched $C_{1-8}$-alkyl, $C_{2-8}$-alkenyl, aryl and a $C_{1-8}$-alkylaryl group.

Suitably groups $R^{1-4}$ are independently a $C_{1-6}$-alkyl group for example methyl or ethyl, or a phenyl group. Preferably q is from 0 to 2, k is from 1 to 3 and g is 0 provided that g+k+q=4.

Examples of suitable alkyl groups include methyl, ethyl, isopropyl, n-propyl, butyl, tert-butyl, n-hexyl, n-decyl, n-dodecyl, cyclohexyl, octyl, iso-octyl, hexadecyl, octadecyl, iso-octadecyl and docosyl. Examples of suitable alkenyl groups include ethenyl, 2-propenyl, cyclohexenyl, octenyl, iso-octenyl, hexadecenyl, octadecenyl, iso-octadecenyl and docosenyl.

$C_{1-6}$-alkoxy refers to a straight or branched hydrocarbon chain having from one to six carbon atoms and attached to an oxygen atom. Examples include methoxy, ethoxy, propoxy, tert-butoxy and n-butoxy.

The term polyol refers to an organic compound particularly with an alkyl chain having two or more hydroxyl groups and specific examples include glycerol, pentaerythritol and dipentaerythritol as well as polyethylene oxide and polypropylene oxide.

The term aryl refers to a five or six membered cyclic, 8-10 membered bicyclic or 10-13 membered tricyclic group with aromatic character and includes systems which contain one or more heteroatoms, for example, N, O or S. Examples of suitable aryl groups include phenyl, pyridinyl and furanyl. Where the term "alkylaryl" is employed herein, the immediately preceding carbon atom range refers to the alkyl substituent only and does not include any aryl carbon atoms. Examples of suitable alkaryl groups include benzyl, phenylethyl and pyridylmethyl.

Compounds in which wherein X is independently selected from $CH_2A$, $[CH_2CH_2NR^1]_pR^2$; $CHCOX_1CH_2COX_2$ and $(CH_2)_eCO$ $Y[CO$ $(CH_2)_eSCH_2CH_2Si(O_{3/2})]_m[CO(CH_2)_e SH]_n$ where A is the residue of an amino acid or derivative or salt of an amino acid of formula $CHNR^1R^2COX_3$ where $R^1$ and $R^2$ are independently selected from hydrogen and $C_{1-12}$ acyl and $X_3$ is selected from OR and $NR^1R^2$, R is selected from hydrogen, metal ion, $C_{1-6}$ alkyl, p is 1 to 20; $X_1$ and $X_2$ are independently selected from OR and $NR^1R^2$; and Y is the residue of polyol having z hydroxyl groups and m+n+1 is less than or equal to z, M is a metal ion derived from a lanthanide, actinide, main group or transition metal and V is an optionally substituted $C_{1-22}$-alkyl, $C_{2-22}$-alkenyl or $C_{2-22}$-alkynyl group or an aryl group; z is an integer from 2 to 10, are preferred.

Preferred polyols include glycerol, pentaerythritol and dipentaerythritol.

Compounds of Formula 1 in which the free valences of the silicate oxygen atoms are saturated by one or more of silicon atoms of other groups of Formula 1, hydrogen, a linear or branched $C_{1-12}$-alkyl group or by end groups $R^3_3M^1O_{1/2}$ or by cross-linking bridge members or by polymer chains $R^3_qM^1(OR^4)_gO_{k/2}$ or $Al(OR^4)_{3-p}O_{h/2}$ or $R^3Al(OR^4)_{2-r}O_{r/2}$; where $M^1$ is Si or Ti in which $R^4$ is a linear or branched $C_{1-12}$, an aryl or $C_{1-12}$-alkylaryl group; and $R^3$ is a linear or branched $C_{1-12}$-alkyl group or an aryl or $C_{1-12}$-alkylaryl group; k is an integer from 1 to 3 and q is an integer from 1 to 2 and g is an integer from 0 to 2; such that g+k+q=4; p is an integer from 1 to 3; and r is an integer from 1 to 2; are preferred.

Where an end group and/or cross linker and or polymer chain is used, it is preferred that the ratio of end groups or cross linker or polymer chains to a+b+c varies from 0 to 99:1, preferably 0.01 to 99:1. Particularly suitable cross linkers or polymer chains are derived from titanium alkoxides, aluminium trialkoxides and alkyl alkoxy silanes. Examples of cross linkers include aluminium triethoxide, aluminium tributoxide and titanium isopropoxide and for polymer chains alkyl alkoxy silanes. The end group, cross linking bridge or polymer chain member is preferably $R^3_3M^1O_{1/2}$, $R^3_2SiOR^4O_{1/2}$, $(R^3)_2SiO_{2/2}$, $TiO_{4/2}$, $R^3TiO_{3/2}$, $(R^3)_2TiO_{2/2}$, $AlO_{3/2}$ or $R^3AlO_{2/2}$. $R^3$ and $R^4$ are preferably $C_{1-4}$-alkyl, especially methyl or ethyl.

The invention also provides novel precursor compounds for formula 1, the precursor being of formula $(R^4O)_3SiCH_2CH_2SX$.

The invention also provides a process of producing the precursor of formula $(R^4O)_3SiCH_2CH_2SX$ comprising reacting a compound of formula $(R^4O)_3SiCH_2\!\!=\!\!CH_2$ with a thiol of formula HS—X where X is as herein defined.

The preparation of compounds of Formula 1 will now be discussed in greater detail. The general procedure used for the production of the compounds of Formula 1 comprises first forming the compounds $(R^4O)_3SiCH_2CH_2SX$ and depending on the reagents and then combining with tetraalkyl orthosilicate and with other compounds such as $(R^4O)_3SiV$, titanium alkoxides, aluminium trialkoxides and alkyl alkoxy silanes, in the desired ratios, in solvent with either dilute acid or base. Alternatively the surfaces of materials such as silica, aluminium oxide or carbon can be treated with $(R^4O)_3SiCH_2CH_2SX$ and if necessary with other compounds such as $(R^4O)_3SiV$, titanium alkoxides, aluminium trialkoxides and alkyl alkoxy silanes to give compounds of Formula 1. These materials can then be subsequently transformed using known chemistry.

There is a lack of simple and effective synthetic methodology for the preparation of functionalised organic or inorganic polymers or materials. For example there is a lack of simple and effective synthetic methodology for the preparation of readily transformed carbonyl, carboxy, thio or hydroxy functionalised organic or inorganic polymers or materials. As a consequence there is a lack of readily available functionalised materials that possess the chemical functionality necessary to remove metal ions held in tightly bound complexes. Given the advantages of inorganic materials such as high thermal stability, fast kinetics and greater solvent compatibility there is a particular need for new simple synthetic methodologies for the preparation of functionalised inorganic materials.

An important desired property of functionalised materials is to be able to transform the functional group, attached to the surface via a stable bond, into different groups using known chemistry. These new functionalised materials can then be used for other applications or to optimise existing applications. A further advantage is that a wide range of different functionalised materials can be made from a limited number of intermediates. However a number of problems are encountered in the chemical transformation of surface attached functional groups. For example very long reaction times are often needed to conduct such chemical transformations of surface attached functional groups. These prolonged reaction conditions often result in the functional group being removed from the surface. In addition those reactions that do proceed very often do not go to completion leading to a mixture of products that cannot be separated. To circumvent these difficulties the inventors designed these new functionalised materials with specific additional functionality to enhance the chemical reactivity of these materials. In addition the inventors believed that this design would enhance the properties of the materials for a number of desired applications. The design involved the use of a neighbouring group to enhance the reactivity of the second functional group.

It is known that free radical reactions involving alkenes may not proceed in high yield or selectivity as, depending on the particular starting materials unwanted dimers and higher tellomers may undesirably be produced for example as disclosed in *Org. Reactions*, Vol. 13, page 218-222 and the references provided therein. In the original 1950's work mono substituted products and not mixtures were the desired target for use as fine chemicals. As a consequence of these side reactions interest in this area of chemistry waned. It has been reported that sulfides can be prepared through the free radical addition of thiols to double bonds. This is described in *Org. Reactions*. Vol. 13, 164-196. The majority of this work concerns the addition of thiols to simple alkyl substituted olefins. For silicon containing olefins there are a small number of examples that include the photochemical catalysed reaction of methyl thioglycolate with trimethoxy vinylsilane reported in *J. Gen. Chem.*, 1976, 46, 1013 to give $(RO)_3Si(CH_2)_2SCH_2CO_2R$. These compounds were investigated for pharmacological activity in a programme on atrane derivatives. Also it has been reported in the *Russ. J. Appl. Chem*, 1999, 72, 610-612 that the radical catalysed reaction of thioglycolic acid, $HSCH_2CO_2H$, to trimethoxy vinylsilane gives a complex mixture which on either acid or neutral treatment does not lead to a polymeric material. Strong base treatment followed by acidification was reported to give a polymeric material described as $[O_{1.5}Si(CH_2)_2SCH_2CO_2H]_n$. The sodium salts of this polymer are capable of removing both silver and gold ions but are ineffective for other metal ions.

Thus it was decided to explore the free radical addition of substituted thiols to vinyl trialkoxy silane to produce functionalised organopolysiloxanes with the desired physical and chemical properties for applications such as scavengers for the removal of unwanted chemical, as materials for solid phase synthesis, as materials for cation and anion recovery and removal, for solid phase purification and extraction, as catalysts and catalyst supports, as chromatography materials and for the immobilisation of bio-molecules.

Compounds such as $(R^4O)_3SiCH_2CH_2SX$ were synthesised via a free radical promoted addition of a thiol HSX to vinyl trialkoxy silane. $R^4$ is a linear or branched $C_{1-22}$-alkyl, $C_{2-22}$-alkenyl or $C_{2-22}$-alkynyl group, aryl or $C_{1-22}$-alkylaryl group. A wide range of free radical initiators can be used for this reaction and preferred are the peroxides and in particular the alkyl peroxides. Addition of a very small amount of the initiator every few hours improves the overall yield. Reaction temperatures between 20-170° C. can be used, though a reaction temperature of between 20-120° C. is preferred. Di-tert-butyl peroxide is the preferred free radical initiator. Reaction times of between 5 minutes to 48 hours have been used with ½ to 2 hours preferred. Known sol-gel technology was used to produce the organopolysiloxanes of Formula 1. The state of the arts of sol-gel technology and the hydrolysis of silicon esters are described by M. A. Brook in *Silicon in Organic, Organometallic and Polymer Chemistry* Chapter 10, page 318, John Wiley & Sons, Inc., 2000, G. A. Scherer in *Sol-gel science: the physics and chemistry of sol-gel processing*, Boston: Academic Press, 1990, and J. D. Wright in *Sol-gel materials: chemistry and applications*, Amsterdam: Gordon & Breach Science Publishers, 2001 and the references contained within. Acids and bases were used to catalyse the hydrolysis of the silicon esters of $(R^4O)_3SiCH_2CH_2SX$ and if necessary with other compounds such as $(R^4O)_3SiV$, and tetraalkyl orthosilicate to produce the organopolysiloxanes of Formula 1.

A range of solvents, well known to those skilled in the art of organic chemistry, can be used to conduct this reaction. Alcohols are the preferred solvents particularly methanol and ethanol. After standing for a period of time the solution can be warmed to speed up the formation of the glass. Ratios, by weight, of the alcohol solvent to the combined weight of the reagents from 100 to 0.01 can be used, with ranges from 2-10 being preferred. A range of acids can be used to aid hydrolysis with hydrochloric acid in concentrations ranging from 0.1 to 4 M being preferred. Hydrochloric acid, 1 molar, was routinely used. Ratios, from 0.000001 to 10, of hydrochloric acid, 1 molar, to the combined weight of the reagents can be used, with ranges from 0.0001 to 1 being preferred. In general the reaction mixture was left to stand at temperatures ranging from 0° C.-120° C. to aid hydrolysis and the formation of the Si—O—Si bonds. Temperatures between 20° C.-90° C. are preferred and warming is continued until all the solvent has evaporated and a clear glass is obtained.

In addition to the groups A, B and C, end groups, cross-linking bridge members or polymer chains such as $(R^3)_3SiO_{1/2}$ or $R^3SiO_{3/2}$ or $(R^3)_2SiO_{2/2}$ or $TiO_{4/2}$ or $R^3TiO_{3/2}$ or $(R^3)_2TiO_{2/2}$ or $AlO_{3/2}$ or $R^3AlO_{2/2}$, where $R^3$ is as defined above, but is preferably methyl or ethyl, or other oxo metals can be added in varying ratios to produce the desired compound of Formula 1. These end groups, cross linking bridge or polymer chain precursors are added at the same time as compounds $(R^4O)_3SiCH_2CH_2SX$ and tetraalkyl orthosilicate and $(R^4O)_3SiV$.

Compounds of Formula 1 can also be prepared by treating a preformed material such as silica, or aluminium oxide or other oxides or carbon with $(R^4O)_3SiCH_2CH_2SX$ and with ($R^4O$)$_3$SiV if required, and with other end groups, cross linkers or polymers chains if required, in varying ratios in a solvent. At the end of the reaction the solid is filtered off and washed extensively with solvents such as water or alcohols to remove any remaining starting materials.

Compounds of Formula 1 where A is CHNR$^1$R$^2$CO$_2$R are similarly prepared by a two step process. The first step is a free radical reaction between a thiol and trimethoxy vinyl silane followed either by a sol gel or coating process described above. For example a free radical reaction involving the correspondingly substituted cysteine and trimethoxyvinyl silane gives (CH$_3$O)$_3$SiCH$_2$CH$_2$SCH$_2$CH(NR$^1$R$^2$)CO$_2$R which on sol gel with tetraethyl orthosilicate or coating preformed silica gave compounds of Formula 1 where A is CHNR$^1$R$^2$CO$_2$R. Another example is the free radical reaction between pentaerythritol tetrakis (2-mercaptoacetate) and trimethoxyvinyl silane to give (CH$_3$O)$_3$SiCH$_2$CH$_2$SCH$_2$CO Y[COCH$_2$SCH$_2$CH$_2$Si(OCH$_3$)$_3$]$_m$[COCH$_2$SH]$_n$ which on sol gel with tetraethyl orthosilicate or coating preformed silica gave compounds of Formula 1 where X is CH$_2$COY [COCH$_2$SCH$_2$CH$_2$Si(O$_{3/2}$)]$_m$[COCH$_2$SH]$_n$. The integers m and n are dependent on the relative amounts of the vinyl trimethoxy silane to the polyol used in the preparation.

Templates to aid the preparation of pores with particular sizes and distributions in compounds of Formula 1 can be added at the sol gel stage. On preparation of the solid organopolysiloxane of Formula 1 these templates can be washed out using known methods.

Compounds of Formula 1 may be linked to a metal complex, for example as a ligand. A further aspect of the invention provides a Compound of Formula 1 further comprising a metal complex M(L)$_j$ where M is derived from a lanthanide, actinide, main group or transition metal with oxidation states ranging from zero to four and L is one or more optionally substituted ligands selected from halide, nitrate, acetate, carboxylate, cyanide, sulfate, carbonyl, imine, alkoxy, triaryl or trialkylphosphine and phenoxy and j is an integer from 0 to 8 and where the compound of Formula 1 is linked to the said metal complex.

Suitably, M is derived from cobalt, manganese, iron, nickel, palladium, platinum, rhodium, with oxidation states ranging from zero to four and L is one or more optionally substituted ligands selected from halide, nitrate, acetate, carboxylate, cyanide, sulfate, carbonyl, imine, alkoxy, triaryl or trialkylphosphine and phenoxy and j is an integer from 0 to 4.

Compounds of Formula 1 have a wide range of uses. The present invention provides a process for treating a feed material comprising contacting a compound of Formula 1 with a feed material:

i) to effect a chemical reaction by catalytic transformation of a component of the feed material to produce a desired product;

ii) to remove a component of the feed material so as to produce a material depleted in the removed component; or iii) to remove an ionic species in the feed material in an ion exchange process.

The feed material may be a continuous stream for example a continuous process reaction feedstock, or may be in the form of a batch of material for discrete treatment. The feed material, for example a waste water or waste process stream, may be treated to selectively remove a components of the feed. The removed component may be an undesirable material in the feed and the process acts to provide a desired composition for the feed material that has been depleted in the selectively removed component after contact with compounds of Formula 1. This process may be used for example in removing unwanted species from a feed material in a pharmaceutical manufacturing or formulation process to improve the purity level of the pharmaceutical product as regards the removed material, for example metal species.

The process may be employed to remove desired species from a feed material for subsequent processing or analysis, for example a biological molecule such as an enzyme, peptide, protein and nucleic acid may be removed from a feed material to enable further processing or analysis of the removed components.

As a consequence of stricter environmental regulations there is a growing requirement for more effective systems for the removal and recovery of cations and anions from a wide spectrum of contaminated solvents, aqueous based wastes and from contaminated waters and contaminated products and pharmaceuticals. Compounds of Formula 1 are very effective at abstracting a wide range of cations and anions from various environments. For cations these include the lanthanides, actinides, main group and transition metals. Anions include arsenates, borates, chromates, permanganates and perchlorates.

Compounds of Formula 1 were designed to have very high affinity for ions and thus be able to remove them from various environments. Such high affinity is required when metal ions are tightly bound to particular functional groups for example in highly polar active pharmaceutical ingredients. The design of compounds of Formula 1 for these applications involves the presence of two or more different ligands to bind strongly to the ion. Depending on the ion to be removed the ligands are designed to be either soft or hard or a combination of both in order to optimise the affinity of the functionalised material for the ion. Furthermore the compounds of Formula 1 have been designed with easily modified functional groups in order to simply find the optimum combination of ligands for specific ion impurities.

For example the products from Examples 9, 10, 12-16, and 24-29 are very effective for the removal of cupric (II) ions from various solutions. Ferrous and ferric ions present in hydroprocessing streams are readily removed using the products from Examples 9, 10 and 24-29. The scavenging of metal ions from strong metal chelates is a major challenge facing the water and associated industries. Examples of such chelates include EDTA, citrates and oxalates. These metals chelates pose a significant health problem due to the their high toxicity. To effectively scavenge the metal ions from these chelates requires functional groups with a higher affinity for the metal ions. This requires a functionalised material with particularly designed range of functionality. Compounds of Formula 1 have been designed to possess a range of functionality to enable the metal ion to be removed from a strong chelating group. As illustrated in Examples 32 and 33 the products from Examples 12-15 are very effective for the removal of cupric (II) ions bound to chelating groups such as EDTA and citrate.

Compounds of Formula 1 can also remove precious metals such as palladium, platinum and rhodium ion as well as nickel (O) and nickel (II) from various different solutions and also bound to functional groups commonly found in active pharmaceutical ingredients such as amides, amines and carboxylic acids. For example treatment of a palladium acetate solution in tetrahydrofuran or dichloromethane with any of the products from Examples 4, 9, 10, 12-16 and 24-29 results in the complete removal of the palladium ions from solution. For solutions containing bis(triphenylphosphine) palladium chloride or acetate, the products from Examples 12-14, and 24-29 are equally effective for its removal. The products from Examples 4, 12-14 and 24-29 are effective for the removal of chlorotris(triphenylphosphine) rhodium (I) from various solutions. The products from Examples 4, 12-142, and 24-29 are effective for the removal of platinum chloride from various solutions. Rhodium (III) is readily removed from various solutions using any of the products from Examples 4, 12-4, and 24-29.

There is a growing use of ruthenium catalysts in the manufacture of complex compounds for a variety of applications. A significant problem encountered with these toxic catalysts is that the metal is bound to the desired compound and can't be readily removed using standard methodologies. Compounds of Formula 1 can also remove ruthenium from various different solutions and also bound to functional groups commonly found in active pharmaceutical ingredients such as amides, amines and carboxylic acids. For example treatment of a ruthenium chloride solution with any of the products from Examples 4, 12, and 24-29 results in the complete removal of the ruthenium ions from solution.

Given their respective catalytic cycles the precious metals are often present in waste steams, solutions or bound to products in more than one oxidation state. Compounds of Formula 1, such as Examples 4, 12, 13, 14 and 24-29 can scavenge these precious metals in their different oxidation states.

Compounds of Formula 1 can be used to remove anions such as arsenates, chromates, permanganates, borates and perchlorates. These anions pose many significant problems to the environment and health. For example toxic chromate anions can be removed using the materials prepared in Example 45 through exchange of the halide anion for chromate. Compounds of Formula 1 can be used, as scavengers, to remove excess inorganic or organic reagents and side products from reactions mixtures or from impure chemical products. In these applications impurities are removed by matching functionality contained in these impurities with specific functionalised materials. For example the amines and polyamine materials prepared in Example 12-16 respectively can readily remove carboxylic acids and mineral acids as well as other acidic reagents from reaction mixtures. The amines and polyamines prepared in Examples 12-16 respectively can remove isocyanates, acid chlorides, aldehydes, sulfonyl halides and chloroformates. The following examples illustrate the scavenging of unwanted organic and inorganic compounds by compounds of Formula 1 but are not intended to limit the scope of their capability. Treatment of solutions containing amines such as benzylamine, hexylamine and 3-methoxypropylamine with 2 to 4 equivalents of an organopolysiloxane carboxylic acid of Formula 1 at room temperature for 1 hour led to the complete removal of the amine. Excess borohydrides such as sodium borohydride can be removed on treatment with the organopolysiloxane carboxylic acid of Formula 1. Toluene sulfonyl chloride, benzoyl chloride and phenyl isocyanate are readily removed using the amides from Examples 12-16.

Unlike the polystyrene based scavengers, organopolysiloxane compounds of Formula 1 can work in all solvents and are not limited in their application to reaction temperatures below 80° C. In addition compounds of Formula 1 do not suffer from swelling and possess the significant advantage of very fast kinetics compared to organic polymers.

Metal salt/complexes of Formula 1 can catalyse a wide range of reactions well known to practitioners of organic and inorganic chemistry. Examples include but not limited to oxidations, reductions, alkylations, carbon-carbon bond formation, polymerisations, hydroformylations, arylations, acylations, isomerisations, alkylations, carboxylations, carbonylations, esterifications, trans-esterifications and rearrangements. These organopolysiloxane compounds of Formula 1 have many advantages for example they possess good thermal and chemical stability and broad solvent compatibility. One of the advantages of these catalysts is that on completion of the reaction they can be simply filtered off and reused. No apparent loss of activity was observed. Thus an important application of the metal derivatives of Formula 1 is their use as heterogeneous catalysts.

Compounds of Formula 1 can also be used for solid phase synthesis through first attachment of the starting material. A number of chemical reactions can then be conducted and in each step purification is facile through simple filtration. At the end of the sequence the desired material is released from the solid phase.

In addition compounds of Formula 1 can be used as materials for solid phase extraction where a desired product is purified through selective retention on the functionalised materials whilst the impurities are removed. The desired material is then subsequently released using a different solvent system.

Compounds of Formula 1 can also be used for the separation or removal of gases, including the removal of malodorous volatile organic compounds. For example the removal of malodorous amines can be achieved with acids prepared in Examples 4 and 9.

Further applications of compounds of Formula 1 include the use as materials for chromatographic separations. For example the materials of Formula 1 can be used in the separation of amines, including optically active amines. Primary amines can be selectively separated from secondary amines using compounds of Formula 1.

Compounds of Formula 1, containing optically active groups such as in the products formed in Examples 4 and 7, can be used as materials for chiral separation.

Compounds of Formula 1 can be used as materials for gel filtration and high speed size-exclusion chromatography as well as for high pressure liquid chromatography and solid phase extraction.

Compounds of Formula 1 can be used both to immobilise biological molecules such as enzymes, polypeptides, proteins and nucleic acids as well as for their separation and purification. In addition nucleic acids immobilised on compounds of Formula 1 can be used for conducting high volume nucleic acid hybridization assays.

Compounds of Formula 1 can be used as anti-microbial agents. The invention also provides an antimicrobial composition comprising a compound of Formula 1 and a carrier.

Compounds of Formula 1 can be applied as thin films onto a variety of surfaces.

The invention will now be described in detail with reference to illustrative examples of the invention.

EXAMPLE 1

A mixture containing trimethoxyvinylsilane (78 ml, 0.51 mol), N acetyl cysteine (81.6 g, 0.5 mol) and di-tert butyl peroxide (10 drops) was stirred at room temperature and then warmed to 115° C. under an atmosphere of nitrogen. The mixture was maintained at this temperature for 4 h during which di-tert butyl peroxide (10 drops) was added every 20 min. The solution was then cooled to room temperature to give (2-trimethoxysilylethyl) N acetyl cysteine.

EXAMPLE 2

A mixture of the product from Example 1 (33.1 g, 0.10 mol) and tetraethyl orthosilicate (62.4 g, 0.3 mol) was dissolved in methanol (200 ml) and 1 M HCl (36 ml) was added with stirring. The mixture was then warmed at 80° C. until the methanol had evaporated and a glass had formed. The glass was crushed and then stirred in refluxing methanol. The material was then dried under reduced pressure of 0.1 mm Hg at 80° C. for 2 h to give a carboxylic acid of Formula 1, where R is OH, $R^1$ is hydrogen, $R^2$=COMe and c=0, as a white powder.

EXAMPLE 3

A mixture of the product from Example 1 (33.1 g, 0.1 mol) and tetraethyl orthosilicate (223 ml, 1.0 mol) was dissolved in methanol (400 ml) and 1 M HCl (90 ml) was added with stirring. The mixture was then warmed at 80° C. until the methanol had evaporated and a glass had formed. The glass was crushed and then stirred in refluxing methanol. The material was then dried under reduced pressure of 0.1 mm Hg at 80° C. for 2 h to give a carboxylic acid as a white powder.

EXAMPLE 4

A mixture of the product from Example 1 (33.1 g,) and silica (70 g, 60-200 microns) in toluene (200 ml) was refluxed for 4 h. After cooling the mixture was filtered and the solid washed with methanol and then dried to give a carboxylic acid of Formula 1, where R is OH, $R^1$ is hydrogen, $R^2$=COMe and c=0, as a white powder.

EXAMPLE 5

A mixture of the product from Example 4 (10.0 g) in distilled water (100 ml) was brought to pH 7 using 1M sodium hydroxide solution. The solid was filtered and washed with water and then methanol and then dried to give a sodium carboxylate of Formula 1 as a white powder.

EXAMPLE 6

A mixture containing trimethoxyvinylsilane (78 ml, 0.51 mol), methyl N acetyl cysteine (88.6 g, 0.5 mol) and di-tert butyl peroxide (10 drops) was stirred at room temperature and then warmed to 115° C. under an atmosphere of nitrogen. The mixture was maintained at this temperature for 4 h during which di-tert butyl peroxide (10 drops) was added every 20 min. The solution was then cooled to room temperature to give (2-trimethoxysilylethyl) methyl N acetyl cysteine.

EXAMPLE 7

A mixture of the product from Example 6 (34.5 g,) and silica (70 g, 60-200 microns) in toluene (200 ml) was refluxed for 4 h. After cooling the mixture was filtered and the solid washed with methanol and then dried to give a methyl ester of Formula 1, where R is $OCH_3$, $R^1$ is hydrogen, $R^2$=COMe and c=0, as a white powder.

EXAMPLE 8

A mixture containing triethoxyvinylsilane (0.51 mol), mercaptosuccinic acid (75 g, 0.5 mol) and di-tert butyl peroxide (10 drops) was stirred at room temperature and then warmed to 140° C. under an atmosphere of nitrogen. The mixture was maintained at this temperature for 4 h during which di-tert butyl peroxide (10 drops) was added every 20 min. The solution was then cooled to room temperature to give (2-trimethoxysilylethyl) mercaptosuccinic acid.

EXAMPLE 9

A mixture of the product from Example 8 (34.0 g,) and silica (70 g, 45-90 microns) in toluene (200 ml) was refluxed for 4 h. After cooling the mixture was filtered and the solid washed with methanol and then dried to give a dicarboxylic acid of Formula 1, where $X^1$ and $X^2$ are hydrogen and c=0, as a white powder.

EXAMPLE 10

A mixture of the product from Example 9 (8.5 g) in distilled water (80 ml) was brought to pH 7 using 1M sodium hydroxide solution. The solid was filtered and washed with water and then methanol and then dried to give a disodium carboxylate of Formula 1 as a white powder.

EXAMPLE 11

A mixture containing trimethoxyvinylsilane (32.13 ml, 0.21 mol), 2-mercapto ethanol (14 ml, 0.2 mol) and di-tert butyl peroxide (10 drops) was warmed to 115° C. under an atmosphere of nitrogen and maintained at this temperature for 1 h. The solution was then cooled to room temperature to give 2-hydroxyethyl, 2-trimethoxysilylethyl sulfide. $^1$H NMR, $CDCl_3$ 3.49 (2H, t, $OCH_2$) and 2.63 (4H, bm, $OCCH_2SCH_2$). A mixture of 2-hydroxyethyl, 2-trimethoxysilylethyl sulfide (14.69 g, 0.065 mol), silica (Grace 70-200 microns, 39.81 g) and water (120 ml) were stirred under gentle reflux for 2 h. Concentrated hydrochloric acid (120 ml) was cooled and the mixture was stirred and refluxed for a further 2 h. After cooling white solid was filtered and then washed well with water and then methanol to give 2-chloroethyl sulfide ethyl silica (47 g) of Formula 1.

EXAMPLE 12

A mixture of the product from Example 11 (34.0 g,) and diethylene triamine (7 g,) in toluene (120 ml) was refluxed for 4 h. After cooling the mixture was filtered and the solid washed with dilute sodium hydroxide solution (0.1M, 50 ml), water and then methanol and dried to give a triamine of Formula 1, where $R^1$ and $R^2$ are hydrogen, p=3 and c=0, as a white powder.

EXAMPLE 13

A mixture of the product from Example 11 (54.0 g,) and triethylene tetra amine (12 g,) in toluene (200 ml) was refluxed for 4 h. After cooling the mixture was filtered and the solid washed with dilute sodium hydroxide solution (0.1M, 50 ml), water and then methanol and dried to give a tetra amine of Formula 1, where $R^1$ and $R^2$ are hydrogen, p=4 and c=0, as a white powder.

EXAMPLE 14

A mixture of the product from Example 11 (62.0 g,) and tetraethylene penta amine (14 g,) in toluene (200 ml) was refluxed for 4 h. After cooling the mixture was filtered and the solid washed with dilute sodium hydroxide solution (0.1M, 50 ml), water and then methanol and dried to give a penta amine of Formula 1, where $R^1$ and $R^2$ are hydrogen, p=5 and c=0, as a white powder.

EXAMPLE 15

A mixture of the product from Example 11 (41.0 g,) and polyethylene amine (average $M_n$ 423, 15 g,) in toluene (200 ml) was refluxed for 4 h. After cooling the mixture was filtered and the solid washed with dilute sodium hydroxide solution (0.1M, 50 ml), water and then methanol and dried to give a poly amine of Formula 1, as a white powder.

EXAMPLE 16

A mixture of the product from Example 11 (32.0 g,) and polyethylene amine (average $M_n$ 600, 16 g,) in methanol (120 ml) was refluxed for 4 h. After cooling the mixture was filtered and the solid washed with dilute sodium hydroxide solution (0.1M, 50 ml), water and then methanol and dried to give a poly amine of Formula 1, as a white powder.

EXAMPLE 17

A mixture of the product from Example 11 (38.0 g,) and 1-methyl piperazine (7 g,) in toluene (100 ml) was refluxed for 4 h. After cooling the mixture was filtered and the solid washed with dilute sodium hydroxide solution (0.1M, 50 ml), water and then methanol and dried to give N-methyl piperazine of Formula 1, as a white powder.

EXAMPLE 18

A mixture of the product from Example 11 (34.0 g,) and 1-(3-aminopropyl)imidazole (9 g,) in toluene (200 ml) was refluxed for 4 h. After cooling the mixture was filtered and the solid washed with dilute sodium hydroxide solution (0.1M, 50 ml), water and then methanol and dried to give an imidazole of Formula 1, as a white powder.

EXAMPLE 19

A mixture of the product from Example 11 (36.0 g,) and 3-aminomethyl pyridine (9 g,) in toluene (200 ml) was refluxed for 4 h. After cooling the mixture was filtered and the solid washed with dilute sodium hydroxide solution (0.1M, 50 ml), water and then methanol and dried to give a pyridine of Formula 1, as a white powder.

EXAMPLE 20

Concentrated hydrochloric acid (8 ml) was added to a stirred mixture of the product from Example 12 (10.0 g,) in water (80 ml) and the resultant mixture was stirred for a further 15 min. The solid was filtered and washed well with distilled water.

EXAMPLE 21

Concentrated hydrochloric acid (8 ml) was added to a stirred mixture of the product from Example 13 (10.0 g,) in water (80 ml) and the resultant mixture was stirred for a further 15 min. The solid was filtered and washed well with distilled water.

EXAMPLE 22

Concentrated hydrochloric acid (8 ml) was added to a stirred mixture of the product from Example 14 (10.0 g,) in water (80 ml) and the resultant mixture was stirred for a further 15 min. The solid was filtered and washed well with distilled water.

EXAMPLE 23

A mixture of the product from Example 10 (0.7 g) in water (30 ml) was treated with an aqueous solution of copper nitrate. The mixture was stirred for 1 h and filtered. The blue solid was filtered, washed well with distilled water and finally with methanol. The material was then dried under reduced pressure of 0.1 mm Hg at 80° C. for 2 h to give the copper salt as a blue powder (0.66 g).

EXAMPLE 24

A mixture of pentaerythritol tetrakis(2-mercaptoacetate) (10.4 g, 0.024 mol) and vinyl trimethoxysilane (5.5 ml, 0.0361 mol) was warmed with stirring at 100° C. for 1 hour and then cooled to room temperature. Toluene (120 ml) and silica (36 g, 45-90 microns) was added and the mixture was stirred and refluxed for 4 h and then cooled to room temperature. The solid was filtered and washed well with distilled water and finally with methanol.

EXAMPLE 25

A mixture of pentaerythritol tetrakis(2-mercaptoacetate) (10.4 g, 0.024 mol) and vinyl trimethoxysilane (6.4 g, 0.0432 mol) was warmed with stirring at 100° C. for 1 hour and then cooled to room temperature. Toluene (120 ml) and silica (36 g, 45-90 microns) was added and the mixture was stirred and refluxed for 4 h and then cooled to room temperature. The solid was filtered and washed well with distilled water and finally with methanol.

EXAMPLE 26

A mixture of pentaerythritol tetrakis(2-mercaptoacetate) (10.4 g, 0.024 mol) and vinyl trimethoxysilane (7.1 g, 0.048 mol) was warmed with stirring at 100° C. for 1 hour and then cooled to room temperature. Toluene (120 ml) and silica (38 g, 45-90 microns) was added and the mixture was stirred and refluxed for 4 h and then cooled to room temperature. The solid was filtered and washed well with distilled water and finally with methanol.

EXAMPLE 27

A mixture of pentaerythritol tetrakis(2-mercaptoacetate) (10.4 g, 0.024 mol) and vinyl trimethoxysilane (10.6 g, 0.072 mol) was warmed with stirring at 100° C. for 1 hour and then cooled to room temperature. Toluene (120 ml) and silica (40 g, 45-90 microns) was added and the mixture was stirred and refluxed for 4 h and then cooled to room temperature. The solid was filtered and washed well with distilled water and finally with methanol.

EXAMPLE 28

A mixture of di pentaerythritol hexakis(2-mercaptoacetate) (13.64 g, 0.02 mol) and vinyl trimethoxysilane (5.92 g, 0.04 mol) was warmed with stirring at 100° C. for 1 hour and then cooled to room temperature. Toluene (100 ml) and silica (40 g, 45-90 microns) was added and the mixture was stirred and refluxed for 4 h and then cooled to room temperature. The solid was filtered and washed well with distilled water and finally with methanol.

EXAMPLE 29

A mixture of di pentaerythritol hexakis(2-mercaptoacetate) (13.64 g, 0.02 mol) and vinyl trimethoxysilane (8.88 g, 0.06 mol) was warmed with stirring at 100° C. for 1 hour and then cooled to room temperature. Toluene (120 ml) and silica (40 g, 45-90 microns) was added and the mixture was stirred and refluxed for 4 h and then cooled to room temperature. The solid was filtered and washed well with distilled water and finally with methanol.

EXAMPLE 30

A mixture of the product from Example 1 (4.9 g) and tetraethyl orthosilicate (41.3 g) and trimethoxy methyl. silane (3.1 g) was dissolved in methanol (160 ml) and 1 M HCl (21 ml) was added with stirring. The mixture was then left at 80° C. until the methanol had evaporated and a glass had formed. The glass was crushed and then stirred in refluxing methanol. The material was then dried under reduced pressure of 0.1 mm Hg at 90° C. for 2 h to give a carboxylic acid of Formula 1, where R is OH, $R^1$ is hydrogen, $R^2$=COMe and V is methyl, as a white powder.

EXAMPLE 31

A mixture of the product from Example 1 (4.8 g) and tetraethyl orthosilicate (41.3 g) and dimethoxy dimethyl silane (4.4 g) was dissolved in methanol (160 ml) and 1 M HCl (22 ml) was added with stirring. The mixture was then left at 80° C. until the methanol had evaporated and a glass had formed. The glass was crushed and then stirred in refluxing methanol. The material was then dried under reduced pressure of 0.1 mm Hg at 80° C. for 2 h to give to give a carboxylic acid of Formula 1, where R is OH, $R^1$ is hydrogen, $R^2$=COMe and with $(CH_3)_2SiO_{2/2}$ as a cross linker, as a white powder.

EXAMPLE 32

The product from Example 14 (0.2 g) was added to a sample (40 ml) of a 20 ppm blue coloured solution of copper ethylenediaminetetraacetate in water. The mixture was agitated gently at room temperature for 2 hours. It was then filtered. Analysis of the filtrate showed that the copper complex had been removed. Examples 12, 13, 15, 16, (0.2 g) were also effective in the above test.

EXAMPLE 33

The product from Example 3 (0.2 g) was added to a sample (40 ml) of a 20 ppm green coloured solution of nickel citrate in water. The mixture was agitated gently at room temperature for 2 hours. It was then filtered. Analysis of the filtrate showed that the nickel complex had been removed. Examples 12, 13, 15, 16 (0.2 g) were also effective in the above test.

EXAMPLE 34

The product from Example 4 (0.06 g) was added to a sample (1 ml) of a 500 ppm dark orange/brown coloured solution of ruthenium trichloride in a mixture of chloroform and dichloromethane. The solution went completely colourless. The mixture was filtered. Analysis of the filtrate showed that the ruthenium had been removed. Examples 12 and 24-29 were equally effective in the above test.

EXAMPLE 35

The product from Example 4 (0.06 g) was added to a sample (1 ml) of a 150 ppm orange coloured solution of chlorotris(triphenylphosphine)rhodium (Wilkinson's catalyst) in chloroform. The solution went completely colourless. The mixture was then filtered. Analysis of the filtrate showed that the rhodium had been removed. Examples 12-16 and 24-29 were equally effective in the above test.

EXAMPLE 36

The product from Example 4 (0.06 g) was added to a sample (1 ml) of a 160 ppm orange coloured solution of palladium acetate in dichloromethane. The solution went completely colourless. The mixture was then filtered. Analysis of the filtrate showed that the palladium had been removed. Examples 12 and 24-29 were equally effective in the above test.

EXAMPLE 37

The product from Example 4 (0.06 g) was added to a sample (1 ml) of a 160 ppm orange coloured solution of tetrakistriphenylphosphine palladium in dichloromethane. The solution went completely colourless. The mixture was then filtered. Analysis of the filtrate showed that the palladium had been removed. Examples 24-29 were equally effective in the above test.

EXAMPLE 38

The product from Example 4 (0.06 g) was added to a sample (1 ml) of a 1300 ppm light yellow coloured solution of potassium tetrachloro platinate in water. The solution went completely colourless. The mixture was then filtered. Analysis of the filtrate showed that the platinum had been removed. Examples 12 and 24-29 were equally effective in the above test.

EXAMPLE 39

The product from Example 24 (0.06 g) was added to a sample (1 ml) of a 2000 ppm green coloured solution of nickel acetate in water. The solution went completely colourless. The mixture was then filtered. Analysis of the filtrate showed that the nickel had been removed. Example 25-29 and 10 were equally effective in the above test.

EXAMPLE 40

The product from Example 4 (0.06 g) was added to a sample (1 ml) of a 1000 ppm yellow coloured solution of ammonium cerium nitrate in water. The solution went completely colourless. The mixture was then filtered. Analysis of the filtrate showed that the cerium had been removed.

EXAMPLE 41

The product from Example 12 (0.2 g) was added to a sample (40 ml) of a 20 ppm light blue coloured solution of copper sulfate in water. The solution was left to agitate gently for 2 hours. The solution went completely colourless. The mixture was then filtered. Analysis of the filtrate showed that the copper had been removed. Examples 9, 10, 13-16 and 24-29 were equally effective in the above test.

EXAMPLE 42

The product from Example 4 (0.06 g) was added to a sample (1 ml) of a 1700 ppm yellow coloured solution of iron nitrate hexahydrate in water. The solution went completely colourless. The mixture was then filtered. Analysis of the filtrate showed that the iron had been removed. Example 9 was equally effective in the above test.

EXAMPLE 43

The product from Example 14 (0.06 g) was added to a sample (1 ml) of a 500 ppm dark blue/grey solution of chromium nitrate nonahydrate in water. The solution went completely colourless. The mixture was then filtered. Analysis of the filtrate showed that the chromium had been removed.

EXAMPLE 44

The product from Example 10 (0.9 g) was added to a sample (5 ml) of a 1000 ppm solution of zinc chloride in water. The mixture was then filtered. Analysis of the filtrate showed that the zinc had been removed.

EXAMPLE 45

The product from Example 20 (0.06 g) was added to a sample (1 ml) of a 250 ppm solution of potassium dichromate in water. The solution went colourless. The mixture was then filtered. Analysis of the filtrate showed that the dichromate had been removed. Examples 21 and 22 were equally effective in the above test.

EXAMPLE 46

A mixture containing para toluenesulfonic acid (0.019 g, 0.1 mmol) and the product from Example 12 (0.54 g, 0.10 mmol) in ether (10 ml) was stirred at room temperature for 1 h and then filtered. The filtrate was concentrated and the residue weighted. Greater then 97% of the para toluenesulfonic acid was removed. Examples 21 and 22 were equally effective in the above test.

EXAMPLE 47

A mixture of anisole (0.035 g, 0.33 mmol) as a marker, benzylamine (0.041 g, 0.38 mmol) and the product from Example 9 (0.65 g, 1.2 mmol) was stirred in CDCl3 (2.5 cm$^3$) at room temperature for 1 h. The mixture was then centrifuged and a $^1$H NMR spectrum of the chloroform solution showed that the benzylamine was completely removed.

EXAMPLE 48

A mixture of anisole (0.02860 g, 0.26 mmol), hexylamine (0.02504 g, 0.25 mmol) and the product from Example 9 (0.5 g, 1.0 mmol) was stirred in CDCl$_3$ (2.5 cm$^3$) at room temperature for 1 h. The mixture was then centrifuged and a $^1$H NMR spectrum of the chloroform solution showed that the hexylamine was completely removed.

EXAMPLE 49

A mixture of anisole (0.031 g, 0.28 mmol), ethyl chloroformate (0.027 g, 0.25 mmol) and the product from Example 12 (0.59 g, 1.11 mmol) was stirred in CDCl$_3$ (2.5 cm$^3$) at room temperature for 1.5 h. The mixture was then centrifuged and a $^1$H NMR spectrum of the chloroform solution showed that the ethyl chloroformate was completely removed. Examples 13-16 were equally effective in this test.

EXAMPLE 50

A mixture of dimethoxyethane (0.022 g, 0.25 mmol), phenyl isocyanate (0.029 g, 0.24 mmol) and the product from Example 12 (0.45 g, 0.97 mmol) was stirred in CDCl$_3$ (2.5 cm$^3$) at room temperature for 1.5 h. The mixture was then centrifuged and a $^1$H NMR spectrum of the chloroform solution showed that the phenyl isocyanate was completely removed. Examples 13-16 were equally effective in this test.

The invention claimed is:
1. A compound of formula 1:

$$[(O_{3/2})SiCH_2CH_2SX]_a [Si(O_{4/2})]_b [Si(O_{3/2}V)]_c$$

wherein X is selected from
CH$_2$A;
[CH$_2$CH$_2$NR$^1$]$_p$R$^2$;
CHCOX$_1$CH$_2$COX$_2$ ; and
(CH$_2$)$_e$CO—Y[CO(CH$_2$)$_e$SCH$_2$CH$_2$Si(O$_{3/2}$)]l$_m$[CO(CH$_2$)$_e$SH]$_n$ and wherein A is the residue of an amino acid or a derivative or a salt of an amino acid of formula

CHNR$^1$R$^2$COX$_3$;

R$^1$ and R$^2$ are independently selected from hydrogen, a C$_{1-22}$ alkyl group, a C$_{1-22}$ acyl group and a C$_{1-22}$ alkaryl group;
X$_3$ is selected from OR, NR$^1$R$^2$, an amino acid and a protein;
R is selected from hydrogen, a metal ion and a C$_{1-22}$ alkyl group;
e is 1 or 2;
p is an integer from 1 to 100;
X$_1$ and X$_2$ are independently selected from OR and NR$^1$R$^2$;
Y is a polyol moiety having z hydroxyl groups wherein z or fewer hydroxyl groups are deprotonated;
m and n are, independently, less than z such that m+n+1 is less than or equal to z and m+n+1 hydroxyl groups of the polyol are deprotonated;
V is a group which is optionally substituted and selected from a C$_{1-22}$-alkyl group, a C$_{2-22}$-alkenyl group, a C$_{2-22}$-alkynyl group, an aryl group, a C$_{1-22}$ alkylaryl sulphide group, a sulfoxide, a sulfone, an amine, a polyalkyl amine, a phosphine and other phosphorous containing group;
the free valences of the silicate oxygen atoms are saturated by one or more of:
a silicon atom of other groups of Formula 1, hydrogen, a linear or branched C$_{1-22}$-alkyl group, an end group R$^3$$_3$M$^1$O$_{1/2}$, a cross-linking bridge member or by a chain R$^3$$_q$M$^1$(OR$^4$)$_g$O$_{k/2}$ or Al(OR$^4$)$_{3-h}$O$_{h/2}$ or R$^3$Al(OR$^4$)$_{2-r}$O$_{r/2}$;
wherein
M$^1$ is Si or Ti;
R$^3$ and R$^4$ are independently selected from a linear or branched C$_{1-22}$ alkyl group, an aryl group and a C$_{1-22}$ alkylaryl group;
k is an integer from 1 to 3, q is an integer from 1 to 2 and m is an integer from 0 to 2 such that g+k+q=4;
h is an integer from 1 to 3; and
r is an integer from 1 to 2;
or an oxo metal bridging systems where the metal is zirconium, boron, magnesium, iron, nickel or a lanthanide;
a, b and c are integers such that the ratio of a:b is from 0.00001 to 100000 and a and b are always greater than 0 and when c is greater than 0, the ratio of c to a+b is from 0.00001 to 100000.
2. A compound as claimed in claim 1 which includes an end group and/or cross linking bridge member and/or polymer chain and wherein the ratio of an end group and/or cross linker and/or polymer chain to a+b+c varies from 0 to 999:1.

3. A compound as claimed in claim 1 that includes an end group derived from a trialkyl or triaryl alkoxysilane or a cross linking bridge member derived from an orthosilicate, a titanium alkoxide or an aluminium trialkoxide or a polymer chain derived from a mono alkyl or mono aryl trialkoxysilane or a di alkyl or di aryl dialkoxysilane.

4. A compound as claimed in claim 3 wherein the one or more end groups or cross linking bridges or polymer chains are selected from $R^3{}_2SiOR^4O_{1/2}$, $R^3{}_3SiO_{1/2}$ or $R^3{}_2SiO_{2/2}$ or $TiO_{4/2}$ or $R^3TiO_{3/2}$ or $R^3{}_2TiO_{2/2}$ or $AlO_{3/2}$ or $R^3AlO_{2/2}$, wherein $R^3$ and $R^4$ are as defined in claim 1.

5. A compound as claimed in claim 4 wherein $R^3$ is independently selected from linear or branched $C_{1-22}$-alkyl, aryl and a $C_{1-22}$ alkylaryl group.

6. A compound as claimed in claim 5 wherein $R^3$ is $C_{1-6}$-alkyl, $C_{2-12}$-alkenyl or aryl.

7. A compound as claimed in claim 1 comprising a metal complex $M(L)_A$ where M is derived from a lanthanide, actinide, main group or transition metal with oxidation states ranging from zero to four and L is one or more optionally substituted ligands selected from halide, nitrate, acetate, carboxylate, cyanide, sulfate, carbonyl, imine, alkoxy, triaryl or trialkylphosphine and phenoxy and j is an integer from 0 to 8 and where the compound of Formula 1 is linked to the said metal complex.

8. A compound as claimed in claim 1 comprising a protonated complex or metal complex $M(L)_j$ where M is derived from cobalt, manganese, iron, nickel, palladium, platinum, rhodium, with oxidation states ranging from zero to four and L is one or more optionally substituted ligands selected from halide, nitrate, acetate, carboxylate, cyanide, sulfate, carbonyl, imine, alkoxy, triaryl or trialkylphosphine and phenoxy and j is an integer from 0 to 4 and where the compound of Formula 1 is linked to the said metal complex.

9. A compound as claimed in claim 1 wherein X is selected from $CH_2A$, $[CH_2CH_2NR^1]_pR^2$; $CHCOX_1CH_2COX_2$ and $(CH_2)_eCOY[CO(CH_2)_eSCH_2CH_2Si(O_{3/2})]_m[CO(CH_2)_eSH]_n$ where A is the residue of an amino acid or derivative or salt of an amino acid of formula $CHNR^1R^2COX_3$ where $R^1$ and $R^2$ are independently selected from hydrogen, $C_{1-12}$ alkyl and $C_{1-12}$ acyl and $X_3$ is selected from OR and $NR^1R^2$; where R is selected from hydrogen, metal ion, $C_{1-12}$ alkyl, P is 1 to 50; $X_1$ and $X_2$ are independently selected from OR and $NR^1R^2$; and Y is the residue of polyol having z hydroxyl groups and m+n+1 is less than or equal to z, M is a metal ion derived from a lanthanide, actinide, main group or transition metal and V is an optionally substituted $C_{1-22}$-alkyl, $C_{2-22}$-alkenyl or $C_{2-22}$-alkynyl group or an aryl group; z is an integer from 2 to 10.

10. A compound as claimed in claim 9 wherein X is selected from $CH_2A$, $[CH_2CH_2NR^1]_pR^2$; $CHCOX_1CH_2COX_2$ and $(CH_2)_eCOY[CO(CH_2)_eSCH_2CH_2Si(O_{3/2})]_m[CO(CH_2)_eSH]_n$ where A is the residue of an amino acid or derivative or salt of an amino acid of formula $CHNR^1R^2COX_3$ where $R^1$ and $R^2$ are independently selected from hydrogen, $C_{1-6}$ alkyl and $C_{1-6}$ acyl and $X_3$ is selected from OR and $NR^1R^2$; where R is selected from hydrogen, metal ion, $C_{1-6}$ alkyl, P is 1 to 20; $X_1$ and $X_2$ are independently selected from OR and $NR^1R^2$; and Y is the residue of polyol having z hydroxyl groups and m+n+1 is less than or equal to z, M is a metal ion derived from a lanthanide, actinide, main group or transition metal and V is an optionally substituted $C_{1-12}$-alkyl, $C_{2-12}$-alkenyl or $C_{2-12}$-alkynyl group or an aryl group; z is an integer from 2 to 10.

11. A compound as claimed in claim 10 containing a metal complex $M(L)_j$ where M is derived from cobalt, manganese, nickel, palladium, platinum, rhodium, with oxidation states ranging from zero to four and L is one or more optionally substituted ligands such as halide, nitrate, acetate, carboxylate, cyanide, sulfate, carbonyl, imine, alkoxy, triaryl or trialkylphosphine and phenoxy and j is an integer from 0 to 4.

12. A compound as claimed in claim 10 wherein A is the residue of an amino acid or derivative or salt of an amino acid of formula $CHNHR^1COX_3$ where $R^1$ is selected from hydrogen, $C_{1-4}$ alkyl and $C_{1-6}$ acyl and $X_3$ is selected from OR and $NR^1H$; where R is selected from hydrogen, metal ion, $C_{1-4}$ alkyl.

13. A compound as claimed in claim 10 wherein X is a branched or linear polyamine $[CH_2CH_2NH]_pH$ where p is an integer from 1 to 10.

14. A compound as claimed in claim 10 wherein X is $(CH_2)_eCOY[CO(CH_2)_eSCH_2CH_2Si(O_{3/2})]_m[CO(CH_{2e},SH]_n$ where Y is the residue of glycerol, penta erythritol and dipentaerythritol having z hydroxyl groups and m+n+1 is less than or equal to z.

15. A compound as claimed in claim 9 wherein the free valences of the silicate oxygen atoms are saturated by one or more of silicon atoms of other groups of Formula 1, hydrogen, a linear or branched $C_{1-6}$ alkyl group or by end groups $R^3{}_3SiO_{1/2}$ or by cross-linking bridge members or by polymer chains $R^3{}_qSiO_{k/2}$ where $R^3$ is a linear or branched $C_{1-4}$ alkyl group; k is an integer from 2 to 3 and q is an integer from 1 to 2; such that k+q=4; and the integers a, b and c are such that i) the ratio of a:b is from 0.00001 to 100,000 and in the formula $A_aB_bC_c$ both A and B are always present, and ii) when C is present the ratio of c to a+b varies from 0.00001 to 100,000 and the ratio of end groups and/or cross linkers and/or polymer chains to a+b+c varies from 0 to 999:1.

16. A compound as claimed in claim 15 wherein a, b and c are such that i) the ratio of a:b is from 0.00001 to 100,000 and in the formula $A_aB_bC_c$ both A and B are always present, and ii) when C is present the ratio of c to a+b varies from 0.00001 to 100,000 and the ratio of end groups and/or cross linkers and/or polymer chains to a+b+c varies from 0 to 999:1.

17. A compound as claimed in claim 15 wherein a, b and c are such that i) the ratio of a:b is from 0.01 to 100 and in the formula $A_aB_bC_c$ both A and B are always present, and ii) when C is present the ratio of c to a+b varies from 0.01 to 100 and the ratio of end groups and/or cross linkers and/or polymer chains to a+b+c varies from 0 to 99:1.

18. A compound of formula 2:

wherein X is selected from
  $CH_2A$;
  $CHCOX_1CH_2COX_2$; and
  $(CH_2)_eCOY[CO(CH_2)_eSCH_2CH_2Si(O_{3/2})]_m[CO(CH_2)_eSH]_n$ wherein A is the residue of an amino acid or a derivative or a salt of an amino acid of formula

$R^1$ and $R^2$ are independently selected from hydrogen, $C_{1-22}$ alkyl group, $C_{1-22}$ acyl group and a $C_{1-22}$ alkaryl group;
$X_3$ is selected from OR, $NR^1R^2$, an amino acid and a protein;
R is selected from hydrogen, a metal ion, a $C_{1-22}$ alkyl group;
e is 1 or 2;
$X_1$ and $X_2$ are independently selected from OR and $NR^1R^2$;
Y is a polyol moiety having z hydroxyl groups wherein z or fewer hydroxyl groups are deprotonated;
m and n are, independently, less than z such that m+n+1 is less than or equal to z; and
m+n+1 hydroxyl groups of the polyol are deprotonated.

19. A process for treating a feedstock comprising contacting a compound as claimed in claim 1 with a feed stream:
   i) to effect a chemical reaction by catalytic transformation of a component of the feed stream to produce a desired product;
   ii) to remove a component of the feed stream from the stream; or
   iii) to remove an ionic species in the feed stream in an ion exchange process.

20. A process as claimed in claim 19 for conducting a carbon-carbon bond formation reaction, an oxidation, reduction, alkylation, polymerisation, hydroformylation, addition, arylation, acylation, isomerisation, alkylation, carboxylation, carbonylation, esterification, trans-esterification or rearrangement reaction.

21. A method of removing or reducing the level of a toxic organic or inorganic compound in a liquid substrate comprising adding the compound of claim 1 to the liquid substrate.

22. The method of claim 21, wherein the liquid substrate is selected from the group consisting of a reaction mixture, waste stream and waste water and wherein the toxic organic or inorganic compound is bound or attached to other organic compounds.

23. A method of removing or reducing the level of platinum, palladium, rhodium, ruthenium, rhenium or nickel metal or ions from one or more reaction mixtures, waste streams or waste waters comprising adding to the one or more reaction mixtures, waste streams or waste waters the compound of claim 1.

24. A method of catalyzing an oxidation, reduction, a carbon-carbon bond formation reaction, addition, alkylation, polymerisation, hydroformylation, arylation, acylation, isomerisation, carboxylation, carbonylation, esterification, trans-esterification or rearrangement reaction in a reaction mixture comprising adding the compound of claim 1 to the reaction mixture.

25. A method of exchanging a cation or an anion in feed material comprising adding the compound of claim 1 to the feed material.

26. A method of immobilizing one or more biological molecules selected from the group consisting of enzymes, peptides, proteins and nucleic acids in a reaction mixture comprising adding the compound of claim 1 to the reaction mixture.

27. An anti-microbial composition comprising the compound of claim 1 and a carrier.

28. A method of reducing microbes in a mixture comprising adding to the mixture the anti-microbial composition of claim 27.

29. A method of modifying the hydrophilicity of a composition comprising adding to the composition the compound of claim 1.

30. A method of performing solid phase synthesis or solid phase extraction and purification of a starting material on a solid phase comprising exposing the starting material to the compound as claimed in claim 1 in the presence of the solid phase.

31. A method of heterogeneous catalysis of one or more chemical transformations in a reaction mixture comprising mixing the reaction mixture with the compound of claim 1.

32. A method of separating or purifying organic, biological or inorganic molecules from gaseous, liquid or solid environments comprising adding to the gaseous, liquid or solid environments the compound of claim 1.

33. A method of chiral separation of a racemic composition comprising mixing with the racemic omposition the compound of claim 1.

34. A gel filtration composition comprising compound of claim 1.

35. The gel filtration composition of claim 34, wherein the gel filtration composition is used for the purification and/or identification of an organic or biological compound.

36. The method of claim 23, wherein the platinum, palladium, rhodium, ruthenium, rhenium or nickel is bound or attached to other organic compounds.

37. A method of flameproofing an article comprising applying to the article the compound of claim 1.

38. A method of reducing static in or on an article comprising applying to the article the compound of claim 1.

39. A method of coating a biomedical device comprising coating the biomedical device with the compound of claim 1.

40. A method of forming a water repellent film on an article comprising applying to the article the compound of claim 1.

41. A size-exclusion composition comprising the compound of claim 1.

42. The size-exclusion composition of claim 41, wherein the size-exclusion composition is used for the purification and/or identification of an organic or biological compound.

43. A chromatographic composition comprising the compound of claim 1.

44. The chromatographic composition of claim 43, wherein the chromatographic composition is used for the purification and/or identification of an organic or biological compound.

* * * * *